US009182348B2

(12) United States Patent
Zubairy et al.

(10) Patent No.: US 9,182,348 B2
(45) Date of Patent: Nov. 10, 2015

(54) RESONANCE FLUORESCENCE LOCALIZATION MICROSCOPY WITH SUB-WAVELENGTH RESOLUTION

(71) Applicants: The Texas A&M University System, College Station, TX (US); King Abdulaziz City for Science and Technology, Riyadh (SA)

(72) Inventors: Muhammad Suhail Zubairy, College Station, TX (US); Zeyang Liao, College Station, TX (US); Mohammad D. Al-Amri, Riyadh (SA)

(73) Assignees: The Texas A&M University System, College Station, TX (US); King Absulaziz City for Science and Technology, Riyadh (SA)

( * ) Notice: Subject to any disclaimer, the term of this patent is extended or adjusted under 35 U.S.C. 154(b) by 275 days.

(21) Appl. No.: 13/763,129

(22) Filed: Feb. 8, 2013

(65) Prior Publication Data
US 2014/0225004 A1    Aug. 14, 2014

(51) Int. Cl.
*G01N 21/64*    (2006.01)

(52) U.S. Cl.
CPC ........ *G01N 21/6458* (2013.01); *G01N 21/6402* (2013.01); *G01N 21/6456* (2013.01)

(58) Field of Classification Search
CPC .......... G01N 21/6456; G01N 21/6404; G01N 21/6402
See application file for complete search history.

(56) References Cited

PUBLICATIONS

Metcalf et al., "Laser cooling and trapping of atoms," published Nov. 16, 2009; Retrieved from Internet [Dec. 19, 2014]; Retrieved from url:<http://info.phys.unm.edu/~ideutsch/classes/phys500s09/downloads/handpubl.pdf>.*

Agarwal, G. S. et al., "Subwavelength atom localization via coherent population trapping," Journal of Physics B: Atomic, Molecular and Optical Physics, 39, Aug. 14, 2006, pp. 3437-3446.

Binnig, G. et al., "Atomic Force Microscope," Physical Review Letters, vol. 56, No. 9, Mar. 3, 1986, pp. 930-934.

Chang, Jun-Tao et al., "Measurement of the separation between atoms beyond diffraction limit," The American Physical Society, Physical Review A, 73, 031803(R), Mar. 10, 2006, 4 pages.

Cohen-Tannoudji, Claude et al., "Dressed-atom description of resonance fluorescence and absorption spectra of a multi-level atom in an intense laser beam," Journal of Physics B: Atomic, Molecular and Optical Physics, vol. 10, No. 3, Sep. 23, 1976, pp. 345-363, printed in Great Britain.

Denk, Winfried et al., "Two-Photon Laser Scanning Fluorescence Microscopy," www.sciencemag.org, Science vol. 248, Apr. 6, 1990, pp. 73-76.

(Continued)

*Primary Examiner* — Yara B Green
(74) *Attorney, Agent, or Firm* — Blank Rome, LLP

(57) ABSTRACT

The resonance fluorescence spectrum of a number of two-level atoms is driven by a gradient coherent laser field. In the weak dipole-dipole interaction region (separation less than $\lambda/50$), a very strong laser field may be applied such that the Rabi frequency is much larger than the dipole-dipole interaction energy. From the spectrum, the positions of each atom may be determined by just a few measurements. This sub-wavelength microscopy scheme is entirely based on far-field technique and it does not require point-by-point scanning, which makes the method more time-efficient. When two atoms are very close to each other (less than $\lambda/50$), the position information for each atom may still be obtained with very high accuracy provided that they are not too close to other atoms. The method may be extended to an arbitrarily large region without requiring more peak laser power and only a few measurements are required.

14 Claims, 4 Drawing Sheets

(56) References Cited

PUBLICATIONS

Dicke, R. H., "Coherence in Spontaneous Radiation Processes," The American Physical Society, Physical Review, vol. 93, No. 1, Jan. 1, 1954, pp. 99-110.

Freedhoff, Helen S., "Collective atomic effects in resonance fluorescence: Dipole-dipole interaction," The American Physical Society, Physical Review A, vol. 19, No. 3, Mar. 1979, pp. 1132-1139.

Gerhardt, I. et al., "Coherent nonlinear single-molecule microscopy," The American Physical Society, Physical Review A, 82, 063823, Dec. 20, 2010, 6 pages.

Gorshkov, Alexey V. et al., "Coherent Quantum Optical Control with Subwavelength Resolution," The American Physical Society, Physical Review Letters, 100, 093005, Mar. 7, 2008, 4 pages.

Hell, Stefan W. et al., "Breaking the diffraction resolution limit by stimulated emission: stimulated-emission-depletion fluorescence microscopy," Optical Society of America, Optics Letters, vol. 19, No. 11, Jun. 1, 1994, pp. 780-782.

Hell, Stefan W. et al., "Ground-state-depletion fluorescence microscopy: a concept for breaking the diffraction resolution limit," Applied Physics B Lasers and Optics, 60, Feb. 15, 1995, pp. 495-497.

Hemmer, Philip R. et al., "Sub-optical resolution of single spins using magnetic resonance imaging at room temperature in diamond," Jan. 25, 2010, 10 pages.

Hettich, C. et al., "Nanometer Resolution and Coherent Optical Dipole Couping of Two Individual Molecules," www.sciencemag. org, Science vol. 298, Oct. 11, 2002, pp. 385-389.

Hofmann, Michael et al., "Breaking the diffraction barrier in fluorescence microscopy at low light intensities by using reversibly photoswitchable proteins," PNAS, vol. 102, No. 49, Dec. 6, 2005, pp. 17565-17569.

Kiffner, M. et al., "Resonant Interferometric Lithography beyond the Diffraction Limit," The American Physical Society, Physical Review Letters, 100, 073602, Feb. 19, 2008, 4 pages.

Klar, Thomas A. et al., "Subdiffraction resolution in far-field fluorescence microscopy," Optical Society of America, Optics Letters, vol. 24, No. 14, Jul. 15, 1999, pp. 954-956.

Lenz, Georg et al., "Resonance fluorescence from two identical atoms in a standing-wave field," The American Physical Society, Physical Review A, vol. 48, No. 4, Oct. 1993, pp. 3365-3374.

Li, Hebin et al., "Optical imaging beyond the diffraction limit via dark states," The American Physical Society, Physical Review A, 78, 013803, Jul. 1, 2008, 6 pages.

Liao, Zeyang et al., "Quantum Lithography beyond the Diffraction Limit via Rabi Oscillations," The American Physical Society, Physical Review Letters, 105, 183601, Oct. 25, 2010, 4 pages.

Rittweger, Eva et al., "STED microscopy reveals crystal colour centres with nanometric resolution," Nature Photonics, vol. 3, Feb. 22, 2009, pp. 144-147.

Rudolph, T. G. et al., "Two-atom resonance fluorescence in running- and standing-wave laser fields," The American Physical Society, Physical Review A, vol. 52, No. 1, Jul. 1995, pp. 636-656.

Strickler, James H. et al., "Two-photon excitation in laser scanning fluorescence microscopy," Developmental Resource for Biophysical Imaging and Optoelectronics, School of Applied and Engineering Physics, SPIE, vol. 1398 CAN-AM Eastern '90, pp. 107-118, Cornell University, Ithaca, NY.

Sun, Qingqing et al., "Subwavelength optical microscopy in the far field," The American Physical Society, Physical Review A, 83, 063818, Jun. 16, 2011, 5 pages.

Yavuz, D. D., et al., "Nanoscale resolution fluorescence microscopy using electromagnetically induced transparency," The American Physical Society, Physical Review A, 76, 041802(R), Oct. 18, 2007, 4 pages.

* cited by examiner

RESONANCE FLUORESCENCE LOCALIZATION MICROSCOPY WITH SUB-WAVELENGTH RESOLUTION

CROSS-REFERENCE TO RELATED APPLICATIONS

None

STATEMENT REGARDING FEDERALLY SPONSORED RESEARCH OR DEVELOPMENT

Not Applicable

BACKGROUND OF THE INVENTION

1. Field of the Invention

This invention relates to optical microscopy. More particularly, it relates to far-field resonance fluorescence localization microscopy.

2. Description of the Related Art Including Information Disclosed Under 37 CFR 1.97 and 1.98

The resolution limit of traditional far-field optical microscopy is about half the wavelength of the light [see, e.g., E. Abbe, Arch. Mikr. Anat. 9, 413 (1873) and L. Rayleigh, Philos. Mag. 47, 81 (1874)]. To achieve better resolution, one must switch to shorter wavelengths (e.g., electron microscopy) which is usually invasive to the system [see, e.g., A. Diaspro (ed), *Nanoscopy and Multidimensional Optical Fluorescence Microscopy* (CRC Press, Boca Raton, 2010)]. Near-field scanning microscopy can obtain optical imaging with sub-diffraction resolution [see, e.g., G. Binnig, C. F. Quate, and C. Gerber, Phys. Rev. Lett. 56, 930 (1986) and C. Hettich et al., Science 298, 385 (2002)], but due to the surface bound nature it is limited in application. Two-photon fluorescence microscopy first was developed to achieve a higher resolution than classical one-photon fluorescence microscopy in the far field [see, e.g., W. Denk, J. H. Strickler, and W. W. Webb, *Science* 248, 73 (1990) and J. H. Strickler and W. W. Webb, Proc. SPIE 1398, 107 (1991)]. Stimulated emission depletion (STED) and the related concept of ground-state depletion microscopy are then developed to overcome the far-field diffraction limit in fluorescence microscopy [see, e.g., S. W. Hell and J. Wichmann, Opt. Lett. 19, 780 (1994) and S. W. Hell and M. Kroug, Appl. Phys. B 60, 495 (1995)]. Space-dependent dark states are also proposed to achieve subwavelength resolution [see, e.g., G. S. Agarwal and K. T. Kapale, J. Phys. B 39, 3437 (2006) and S. Bretschneider, C. Eggeling, and S. W. Hell, Phys. Rev. Lett. 98, 218103 (2007)]. However, realization of these schemes is based on point-by-point scanning and is time consuming. Coherent Rabi oscillations may also be employed to break the diffraction limit [see, e.g., Z. Liao, M. Al-Amri, and M. S. Zubairy, Phys. Rev. Lett. 105, 183601 (2010) and C. Shin et al., J. Lumin. 130, 1635 (2010)], but the effect of dipole-dipole interaction has not been well discussed. Another method based on resonance fluorescence is able to measure the separation of two interacting atoms with subwavelength resolution [see, e.g., J-T Chang, J. Evers, M. O. Scully, and M. S. Zubairy, Phys. Rev. A 73, 031803(R) (2006) and Q. Sun, M. Al-Amri, M. O. Scully, and M. S. Zubairy, Phys. Rev. A 83, 063818 (2011)].

A question remains whether the locations of multiple atoms can be determined with sub-wavelength resolution even when dipole-dipole interaction is involved.

BRIEF SUMMARY OF THE INVENTION

An evaluation of the resonance fluorescence spectrum of a number of two-level atoms driven by a gradient coherent laser field shows that the positions of atoms can be determined from the spectrum even when the atoms locate within the sub-wavelength range and the dipole-dipole interaction is significant. This far-field resonance fluorescence localization microscopy method does not require point-by-point scanning and is therefore more time-efficient. The present invention also includes a method to extract the position information in an extended region without requiring additional peak laser power. One particular embodiment of the invention is a method that permits 2D imaging.

BRIEF DESCRIPTION OF THE SEVERAL VIEWS OF THE DRAWING(S)

DETAILED DESCRIPTION OF THE INVENTION

The present invention utilizes collective resonance fluorescence to provide the spatial information of a multi-atom system. With this system, far-field resonance fluorescence localization microscopy (RFLM) can be performed with sub-wavelength resolution.

General Formalism for N-Atom Resonance Fluorescence Localization Microscopy

Figure 1:
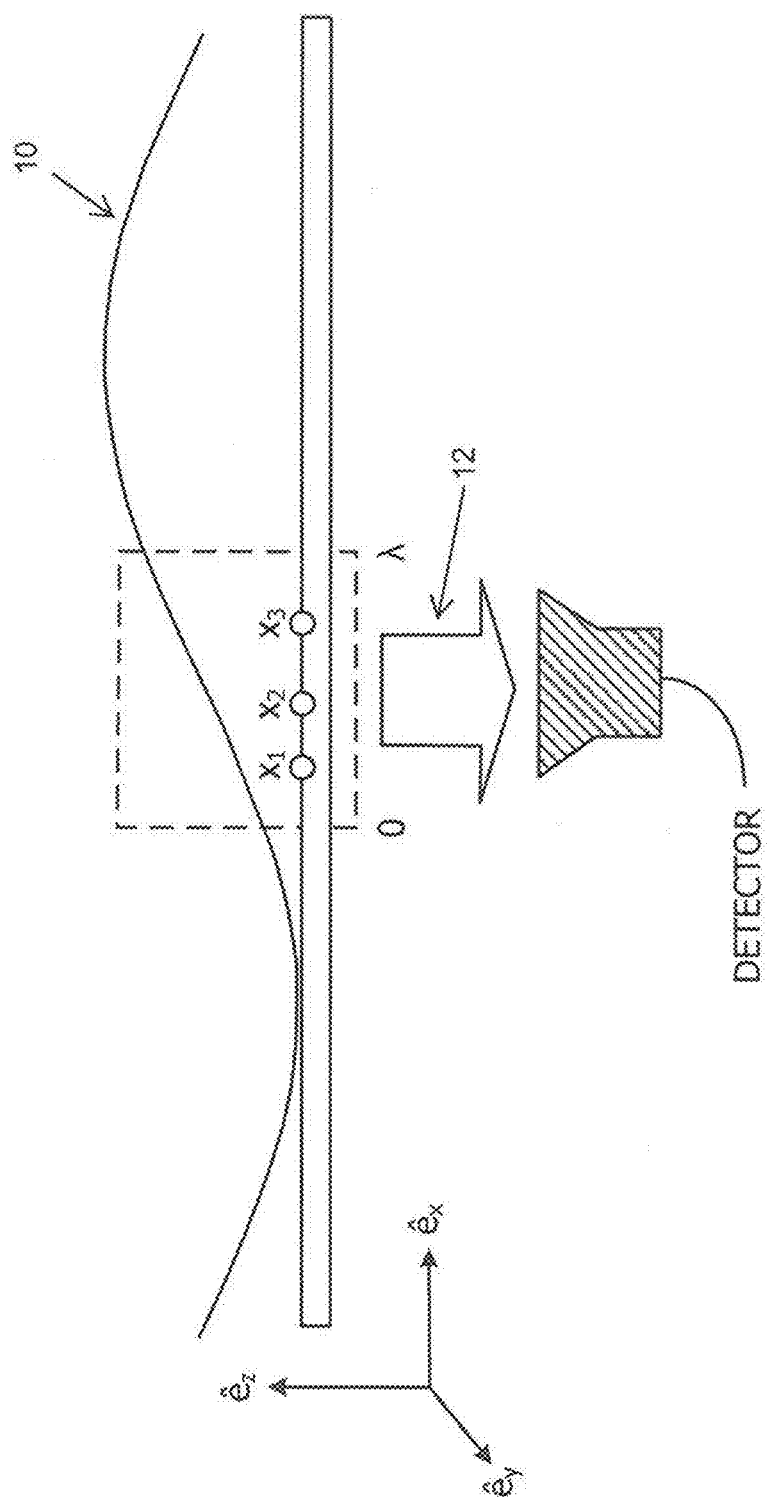
FIG. 1 depicts a scheme for resonance fluorescence microscopy wherein $x_i$ is the position of the ith atom.

For simplicity, first consider identical atoms located in a line along the x axis. Such a configuration is illustrated in FIG. 1. Two, strong, linearly-polarized laser fields with wavelength $\lambda$ shine on these atoms from opposite directions and form a standing wave 10. Assume that the polarization orientation is in $\hat{y}$ direction and the frequency is resonant with the two-level atoms. Also assume that the atoms do not move and they locate within one wavelength. This assumption is valid for the following types of situations: atoms that are trapped by an optical lattice, quantum dots, NV-centers in diamond and the like. The standing wave may be stretched where the sample is located within the approximately linear region between node and anti-node [see, e.g., Z. Liao, M. Al-Amri, and M. S. Zubairy, Phys. Rev. Lett. 105, 183601 (2010) and A. V. Gorshkov, L. Jiang, M. Greiner, P. Zoller, and M. D. Lukin, Phys. Rev. Lett. 100, 093005 (2008)]. In this region, $E(x)=E_0 x/\lambda$. The resonance fluorescence photons 12 emitted by the system may be monitored with a detector in the $\hat{z}$ direction. The resonance fluorescence spectrum encodes the spatial information of the systems from which the position of each atom can be determined.

The Hamiltonian of the system and the field is:

$$H = H_A + H_F + H_{AF} + H_{dd}, \quad (1)$$

where $H_A = \hbar\omega_0 \sum_{i=1}^{N} S_i^z$ is the energy of the atoms, with $\omega_0$ being the level separation and $S_i^z$ is the z component of the spin operator [see, e.g., J-T Chang, J. Evers, M. O. Scully, and M. S. Zubairy, Phys. Rev. A 73, 031803(R) (2006) and T. G.

Rudolph, Z. Ficek, and B. J. Dalton, Phys. Rev. A 52, 636 (1995)]. $H_F=\hbar\omega_0 a^\dagger a$ is the total energy of the photons, where $a(a^\dagger)$ is the annihilation (creation) operator of the photon; $H_{AF}=(\hbar/2)\Sigma_{i=1}^N g_i(S_i^+ a + S_i^- a^\dagger)$ is the interaction between the atoms and the field, with $S_i^+(S_i^-)$ being the raising (lowering) operator on the ith atom, and coupling constant $g_i = g x_i/\lambda$ and $g = \mu(2\omega_0/\hbar\epsilon_0 V)^{1/2}$ ($\mu$ is the transition dipole moment between ground state and excited state); $H_{dd} = \hbar\Sigma_{i\neq j}\Omega_{ij}(S_i^+ S_j^- + S_i^- S_j^+)$ is the dipole-dipole interaction energy. All transition dipole moments are polarized in the y direction and the dipole-dipole interaction energy $\Omega_{ij}$ is given by:

$$\Omega_{ij} = \frac{3\gamma}{4}\left[-\frac{\cos(kx_{ij})}{kx_{ij}} + \frac{\sin(kx_{ij})}{(kx_{ij})^2} + \frac{\cos(kx_{ij})}{(kx_{ij})^3}\right], \quad (2)$$

with $2\gamma = 4\omega_0^3 d_0^2/(3\hbar c^3)$ being the single-atom spontaneous decay rate, $k = \omega_0/c$ (c is speed of light) and $x_{ij}$ is the distance between atoms [see, e.g., Z. Ficek and S. Swain, *Quantum Interference and Quantum Coherence: Theory and Experiment* (Springer, N.Y., 2004)]. The Rabi frequency for the ith atom is given by $\Omega_i = g_i\sqrt{n}$ (or $\mu E_0 x_i/\hbar\lambda$) where n is the photon number.

For $\Omega_i \gg \Omega_{ij}$

Figure 2:
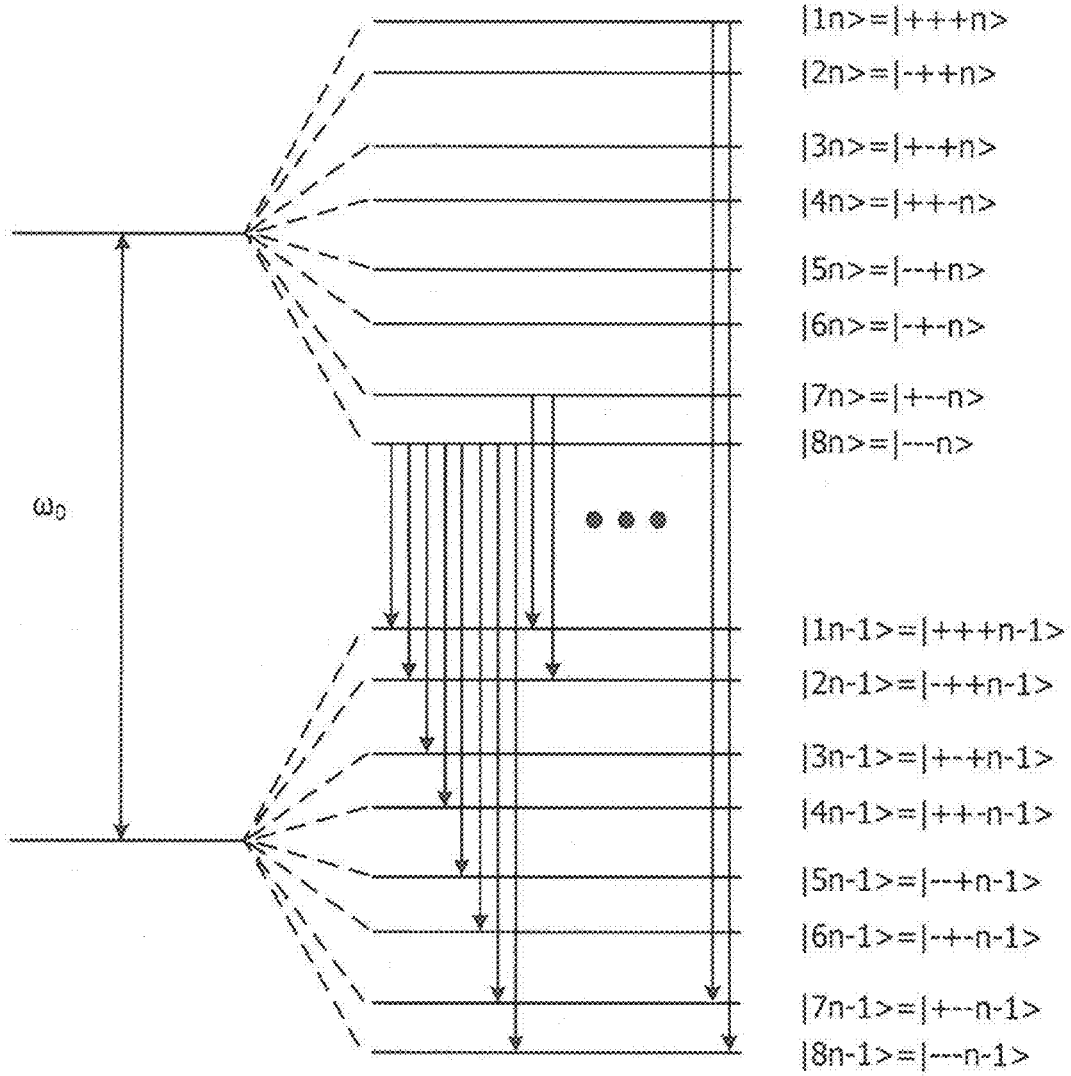
FIG. 2 is a dressed state picture for three interacting atoms. $|\pm\pm\pm n\rangle = (|bn_1\rangle \pm |an_1-1\rangle) \otimes (|bn_2\rangle \pm |an_2-1\rangle) \otimes (|bn_3\rangle \pm |an_3-1\rangle)$ where $n_1+n_2+n_3=n$.

If the dipole-dipole interaction energy is not very strong, a strong laser field may be applied such that $\Omega_i \gg \Omega_{ij}$. In this case, the collective resonance fluorescence spectrum of a multi-atom system may be analytically evaluated based on a dressed state picture [see, e.g., C. Cohen-Tannoudji and S. Reynaud, J. Phys. B: Atom. Molec. Phys. 10, 345 (1977) and H. S. Freedhoff, Phys. Rev. A 19, 1132 (1979)]. Let $H_0 = H_A + H_F + H_{AF}$ and treat $H_{dd}$ as a perturbation term. The eigenvalues and eigenfunctions of $H_0$ are given by:

$$E_{\alpha,n}^0 = \left(n - \frac{N}{2}\right)\hbar\omega_0 + \frac{\hbar}{2}\sum_{i=1}^N \chi_i^\alpha \Omega, \quad (3)$$

$$|\alpha, n\rangle = \frac{1}{\sqrt{2^N}}(|b^N, n\rangle + \sum_{i=1}^N \chi_i^\alpha |a_i b^{N-1}, n-1\rangle + \sum_{i\neq j} \chi_i^\alpha \chi_j^\alpha |a_i a_j b^{N-2}, n-2\rangle + \ldots + \prod_{i=1}^N \chi_i^\alpha |a^N, n-N\rangle),$$

where N is the number of atoms, $\alpha = 1, 2, \ldots, 2^N$, $|a_i b^{N-1}\rangle$ means that ith atom is in the excited state $|a\rangle$ while other N−1 atoms are in the ground state $|b\rangle$, and $\chi_i^\alpha$ is a constant which can be either +1 or −1. Counting the dipole-dipole interaction term as a perturbation, the eigenenergy is shifted by $$\Delta_{\alpha,n} = \frac{\hbar}{2}\sum_{i\neq j}\chi_i^\alpha\chi_j^\alpha\Omega_{ij} \quad (4)$$

and the correction to zeroth order eigenfunction is of the order of $\Omega_{ij}/\Omega_i$ which can be neglected. The sublevel energy $E_{\alpha,n} = E_{\alpha,n}^0 + \Delta_{\alpha,n}$. The pictorial energy level for the dressed state picture is shown in FIG. 2. Coupling of the dressed states to the vacuum results in the system's cascade down the ladder from the α state of one multiplet to the β state of the adjacent multiplet [see, e.g., C. Cohen-Tannoudji and S. Reynaud, J. Phys. B: Atom. Molec. Phys. 10, 345 (1977)]. The corresponding transition frequency is $\omega_{\alpha\beta} = (E_{\alpha,n} - E_{\beta,n-1})/\hbar$, where $\alpha, \beta = 1, 2, \ldots, 2^N$.

The spectrum of resonance fluorescence can be evaluated by:

$$S(\omega) \propto Re\left[\int_0^\infty d\tau e^{i\omega\tau}\lim_{t\to\infty}\langle D^+(t)D^-(t+\tau)\rangle\right], \quad (5)$$

where $D^+$ and $D^-$ are the raising and lowering parts of the total atomic dipole operator [see, e.g., C. Cohen-Tannoudji and S. Reynaud, J. Phys. B: Atom. Molec. Phys. 10, 345 (1977) and H. S. Freedhoff, Phys. Rev. A 19, 1132 (1979)]. The lowering part may be written as $D^- = \Sigma_{\alpha\beta n} d_{\alpha\beta}^- |\beta, n-1\rangle\langle\alpha, n| = \Sigma_{\alpha\beta}D_{\alpha\beta}^-$, where $d_{\alpha\beta}^-$ is the dipole matrix element of the transition from $|\alpha, n\rangle$ to $|\beta, n-1\rangle$ and it is defined by $d_{\alpha\beta}^- = \langle\beta, n-1|\Sigma_{i=1}^N S_i^-|\alpha, n\rangle$ and $D_{\alpha\beta}^- = \Sigma_n d_{\alpha\beta}^- |\beta, n-1\rangle\langle\alpha, n|$.

The two-time correlation function in Eq. (6) may be written as:

$$\langle D^+(t)D^-(t+\tau)\rangle = \Sigma_{\alpha\neq\beta}\langle D^+(t)D_{\alpha\beta}^-(t+\tau)\rangle + \Sigma_\alpha\langle D^+(t)D_{\alpha\alpha}^-(t+\tau)\rangle \quad (6)$$

where the first term corresponds to the sideband spectrum while the second term corresponds to the central peak. According to the quantum regression theorem [see, e.g., M. O. Scully and M. S. Zubairy, *Quantum Optics* (Cambridge University Press, Cambridge, 1997)], the two-time correlation function $\langle D^+(t)D_{\alpha\beta}^-(t+\tau)\rangle$ satisfies the same equation of motion as the single time average $\langle D_{\alpha\beta}^-(t)\rangle$. The dynamics of $\langle D_{\alpha\beta}^-(t)\rangle$ can be calculated from the master equation:

$$\frac{d\langle D_{\alpha\beta}^-(t)\rangle}{dt} = d_{\alpha\beta}^-\frac{d\rho_{\alpha\beta}}{dt} = d_{\alpha\beta}^-\left\{\frac{-i}{\hbar}[H,\rho]_{\alpha\beta} - (L\rho)_{\alpha\beta}\right\} \quad (7)$$

where $\rho_{\alpha\beta}^- = \langle\alpha, n|\rho|\beta, n-1\rangle$, $L = \Sigma_{i,j=1}^N \gamma_{ij}(S_i^+ S_j^-\rho + \rho S_i^+ S_j^- - 2S_j^-\rho S_i^+)$ is the relaxation operator with $\gamma_{ii}$ being the decay rate of atom i and $\gamma_{ij}$ being the cross damping rate. For the sidebands, one may expand $(L\rho)_{\alpha\beta} = \Gamma_{\alpha\beta}\rho_{\alpha\beta} + \ldots$ and, from Eq. (8), one obtains:

$$\frac{d}{dt}\langle D_{\alpha\beta}^-(t)\rangle \simeq (i\omega_{\alpha\beta} - \Gamma_{\alpha\beta})\langle D_{\alpha\beta}^-(t)\rangle, \quad (8)$$

where the non-resonance terms on the right hand side in the secular approximation have been neglected. For the central peak, as all $|\alpha, n\rangle \to |\alpha, n-1\rangle$, $\alpha = 1, \ldots, 2^N$ have the same transition frequency, they couple to each other and one may expand $(L\rho)_{\alpha\alpha} = \Sigma_\beta \Gamma_{\alpha\beta}'\rho_{\beta\beta} + \ldots$. From Eq. (8) one obtains:

$$\frac{d}{dt}\langle D_{\alpha\alpha}^-(t)\rangle = i\omega_0\langle D_{\alpha\alpha}^-(t)\rangle - d_{\alpha\alpha}^-\sum_\beta \Gamma_{\alpha\beta}'\frac{\langle D_{\beta\beta}^-(t)\rangle}{d_{\beta\beta}^-}. \quad (9)$$

According to the quantum regression theorem and Eq. (6), the spectrum is given by:

$$S(\vec{R},\omega) = S^0(\omega) + S^\pm(\omega) \propto \quad (10)$$

-continued $$Re\left[\int_0^\infty d\tau e^{i(\omega-\omega_0)\tau}\sum_{\alpha,\beta}d_{\alpha\alpha}^-(e^{-\Gamma'\tau})_{\alpha\beta}d_{\beta\beta}^+\right]+\sum_{\alpha\neq\beta}\frac{|d_{\alpha\beta}^-|^2\Gamma_{\alpha\beta}}{(\omega-\omega_{\alpha\beta})^2+\Gamma_{\alpha\beta}^2},$$

where the first term yields the central peak spectrum and the second term gives the sideband spectrum.

For the zeroth order wavefunction (Eq. (4) or equivalently Eq. (21)), the transition dipole is given by:

$$d_{\alpha\beta}^- = \frac{1}{2^N}\sum_{i=1}^N\left\{\chi_i^\beta\prod_{k\neq i}\left[1+\chi_k^\alpha\cdot\chi_k^\beta\right]\right\}. \quad (11)$$

There are three possible cases:
Case 1. $\beta=\alpha$, $d_{\alpha\beta}^-=\Sigma_{i=1}^N\chi_i^\alpha/2$ which contributes to the central peak $\omega=\omega_0$;
Case 2. $\beta=\alpha^p$ ($\alpha^p$ is a state such that $E_\alpha^0$ and $E_{\alpha^p}^0$ have different sign only in pth term), $d_{\alpha\beta}^-=\chi_p^\alpha/2$ which contributes to the sidebands $$\omega_{\alpha\alpha^p}=\omega_0+\chi_p^\alpha\Omega_p+\Sigma_{k\neq p}\chi_p^\alpha\chi_k^\alpha\Omega_{pk}; \quad (12)$$

From this equation, it is apparent that the positive sideband peaks can be divided into N groups: $\Omega_p+\Sigma_{k\neq p}\pm\Omega_{pk}$, p=1, ..., N. Averaging over the frequencies of each group provides the Rabi frequencies $\Omega_p$ from which the positions of the atoms may be determined. The error is on the order of $\Omega_{ij}^2/\Omega_i^2\ll1$. This is the method of the present invention for optical microscopy. In an experiment, it may not be known which peak belongs to which group. However, if the gradient of laser field is changed [by an amount], the relative Rabi frequencies for different atoms change which causes the separations between different groups of spectrum shift. Because the dipole-dipole interactions do not change, the splitting between peaks belong to the same group will not change. From this phenomena, peaks belonging to different groups can be identified.

Case 3. $\alpha\neq\beta$ and more than one term of $E_\alpha^0$ and $E_\beta^0$ have different signs, $d_{\alpha\beta}^-=0$ which corresponds to the forbidden transition.

The method described above is valid under the conditions: $\Omega_i\gg\Omega_{ij}$ and $|\Omega_i-\Omega_j|-2\Omega_{ij}\gg\gamma$. Assuming that $\gamma\sim10^8$ Hz and the maximum Rabi frequency is $10^{13}$ Hz, then the smallest distance that can be resolved using this method is about $\lambda/50$.

For $\Omega_{ij}\gg\Omega_i$

When there are two atoms in the sample whose distance is very close (e.g. $r_{ij}<\lambda/50$), the condition $\Omega_i\gg\Omega_{ij}$ cannot be satisfied. The positions of these two atoms cannot be localized based on the method described above. However, there are ways to extract the position information of the two atoms if they are far away from other atoms (e.g., greater than $\lambda/10$). In this case a weak gradient field may be applied such that $\Omega_i$, $\Omega_j\ll\Omega_{ij}$. If Rabi frequency $\Omega_i\sim\gamma$, there are only two sideband peaks located at $\omega_0\pm\Omega_{ij}$ [see, e.g., J-T Chang, J. Evers, M. O. Scully, and M. S. Zubairy, Phys. Rev. A 73, 031803(R) (2006) and T. G. Rudolph, Z. Ficek, and B. J. Dalton, Phys. Rev. A 52, 636 (1995)]. Therefore, the dipole-dipole interaction energy $\Omega_{ij}$ can be determined from the resonance fluorescence spectrum. According to Eq. (2), the distance $r_{ij}$ between these two, close atoms can then be determined.

In one experiment, the gradient field strength was increased to a medium value (for example $\sim100\gamma$) which is still much less than dipole-dipole interaction energy. At this point, each sideband peak split into two peaks [see, id.]. For a positive sideband, it splits into two peaks:

$$\omega_+^1 = \omega_0 + \Omega_{ij} + \frac{\Omega_i\Omega_j)^2}{2\Omega_{ij}}, \quad (13)$$

$$\omega_+^2 = \omega_0 + \Omega_{ij} + \frac{\Omega_i\Omega_j}{\Omega_{ij}}. \quad (14)$$

From each equation and the relationship between $\Omega_i$ and $\Omega_j$, a value for the positions $r_i$ and $r_j$ can be calculated. Because there are two equations, there may be two results. One of the results may be used as the position[s] of the two atoms or the two results may be averaged to obtained the positions of the two atoms.

Linewidth

In general, the linewidth of the emitted radiation is difficult to calculate exactly. However, the linewidth may be evaluated approximately in some cases (discussed infra). From Eq. (2), when the distance between two atoms is about $\lambda/10$, the dipole-dipole interaction energy is comparable to the linewidth of the sideband spectrum of the independent atoms. Therefore, $\lambda/10$ may be set as a threshold and the linewidth evaluated. First, when all the atoms have distances much larger than $\lambda/10$, the dipole-dipole interaction energies are much smaller than the sideband spectrum linewidth of independent atoms and the dipole-dipole interaction energies may be neglected. For independent atoms, the linewidth of the sideband spectrum is $3\gamma/2$ [see, e.g., H. S. Freedhoff, Phys. Rev. A 19, 1132 (1979) and M. O. Scully and M. S. Zubairy, *Quantum Optics* (Cambridge University Press, Cambrige, 1997)], i.e., $\Gamma_{\alpha\beta}=3\gamma/2$ in Eq. (11). Second, when all the atoms have distances much smaller than $\lambda/10$, all dipole-dipole interaction energies $\Omega_{ij}$ are larger than $3\gamma/2$ and the overlapped sideband spectrum splits. One can calculate $(L\rho)_{\alpha\beta}\approx(N/2+1)\gamma\rho_{\alpha\beta}+...$, from which it may be seen that $\Gamma_{\alpha\beta}\approx(N/2+1)\gamma$. The spectrum width is about $(N/2+1)\gamma$ which is similar to superradiance [see, e.g., R. H. Dicke, Phys. Rev. 93, 99 (1954)].

For the general case wherein some atoms have distances larger than $\lambda/10$ and some atoms have distances smaller than $\lambda/10$, the resonance fluorescence has the same transition frequencies but a different linewidth which is about $(N_{eff}+2)\gamma/2$ where $N_{eff}$ is the average number of atoms which couple to each other and its value is between 1 and N.

Three-Atom Example

In the following, the resonance fluorescence spectrum of a three-atom system is solved numerically to demonstrate how this localization microscopy works. The dressed state picture is shown in FIG. 2. From Eq. (3), the eigenvalues of the system are:

$$E_{1n} = \left(n-\frac{3}{2}\right)\hbar\omega_0 + \frac{\hbar}{2}(\Omega_1+\Omega_2+\Omega_3+\Omega_{12}+\Omega_{13}+\Omega_{23})$$

$$E_{2n} = \left(n-\frac{3}{2}\right)\hbar\omega_0 + \frac{\hbar}{2}(-\Omega_1+\Omega_2+\Omega_3-\Omega_{12}-\Omega_{13}+\Omega_{23})$$

$$E_{3n} = \left(n-\frac{3}{2}\right)\hbar\omega_0 + \frac{\hbar}{2}(\Omega_1-\Omega_2+\Omega_3-\Omega_{12}+\Omega_{13}-\Omega_{23})$$

$$E_{4n} = \left(n-\frac{3}{2}\right)\hbar\omega_0 + \frac{\hbar}{2}(\Omega_1+\Omega_2-\Omega_3+\Omega_{12}-\Omega_{13}-\Omega_{23})$$

$$E_{5n} = \left(n-\frac{3}{2}\right)\hbar\omega_0 + \frac{\hbar}{2}(-\Omega_1-\Omega_2+\Omega_3+\Omega_{12}-\Omega_{13}-\Omega_{23})$$

$$E_{6n} = \left(n-\frac{3}{2}\right)\hbar\omega_0 + \frac{\hbar}{2}(-\Omega_1+\Omega_2-\Omega_3-\Omega_{12}+\Omega_{13}-\Omega_{23})$$

$$E_{7n} = \left(n - \frac{3}{2}\right)\hbar\omega_0 + \frac{\hbar}{2}(\Omega_1 - \Omega_2 - \Omega_3 - \Omega_{12} - \Omega_{13} + \Omega_{23})$$

$$E_{8n} = \left(n - \frac{3}{2}\right)\hbar\omega_0 + \frac{\hbar}{2}(-\Omega_1 - \Omega_2 - \Omega_3 + \Omega_{12} + \Omega_{13} + \Omega_{23})$$

For weak dipole-dipole interactions, according to Eq. (12) the nonzero transition dipoles are: $d_{11}^\pm = 3/2$, $d_{22}^\pm = d_{33}^\pm = d_{44}^\pm = 1/2$, $d_{55}^\pm = d_{66}^\pm = d_{77}^\pm = -1/2$, $d_{88}^\pm = -3/2$; $d_{12}^- = d_{13}^- = d_{14}^- = d_{25}^- = d_{26}^- = d_{35}^- = d_{37}^- = d_{47}^- = d_{58}^- = d_{68}^- = d_{78}^- = 1/2$; $d_{21}^- = d_{31}^- = d_{41}^- = d_{52}^- = d_{62}^- = d_{53}^- = d_{73}^- = d_{74}^- = d_{85}^- = d_{86}^- = d_{87}^- = -1/2$. One may also calculate $(L\rho) = \rho_{\alpha\alpha} = (3\gamma/2)\rho_{\alpha\alpha} - (\gamma/2)\Sigma_{\alpha'}\rho_{\alpha'\alpha'}$ where $\alpha \to \alpha'$ is allowed sideband transition. For example, if $\alpha = 1$, then $\alpha' = 2, 3, 4$. Thus, $$\Gamma' = \frac{\gamma}{2}\begin{pmatrix} 3 & -1 & -1 & -1 & 0 & 0 & 0 & 0 \\ -1 & 3 & 0 & 0 & -1 & -1 & 0 & 0 \\ -1 & 0 & 3 & 0 & -1 & 0 & -1 & 0 \\ -1 & 0 & 0 & 3 & 0 & -1 & -1 & 0 \\ 0 & -1 & -1 & 0 & 3 & 0 & 0 & -1 \\ 0 & -1 & 0 & -1 & 0 & 3 & 0 & -1 \\ 0 & 0 & -1 & -1 & 0 & 0 & 3 & -1 \\ 0 & 0 & 0 & 0 & -1 & -1 & -1 & 3 \end{pmatrix}$$

From Eq. (9), one may obtain the central peak spectrum:

$$S^0(\vec{R}, \omega) \propto \frac{3\gamma}{2}\left[\frac{1}{(\omega - \omega_0)^2 + \gamma^2} + \frac{18}{(\omega - \omega_0)^2 + 4\gamma^2} + \frac{9}{(\omega - \omega_0)^2 + 9\gamma^2}\right]. \quad (15)$$

Figure 3:
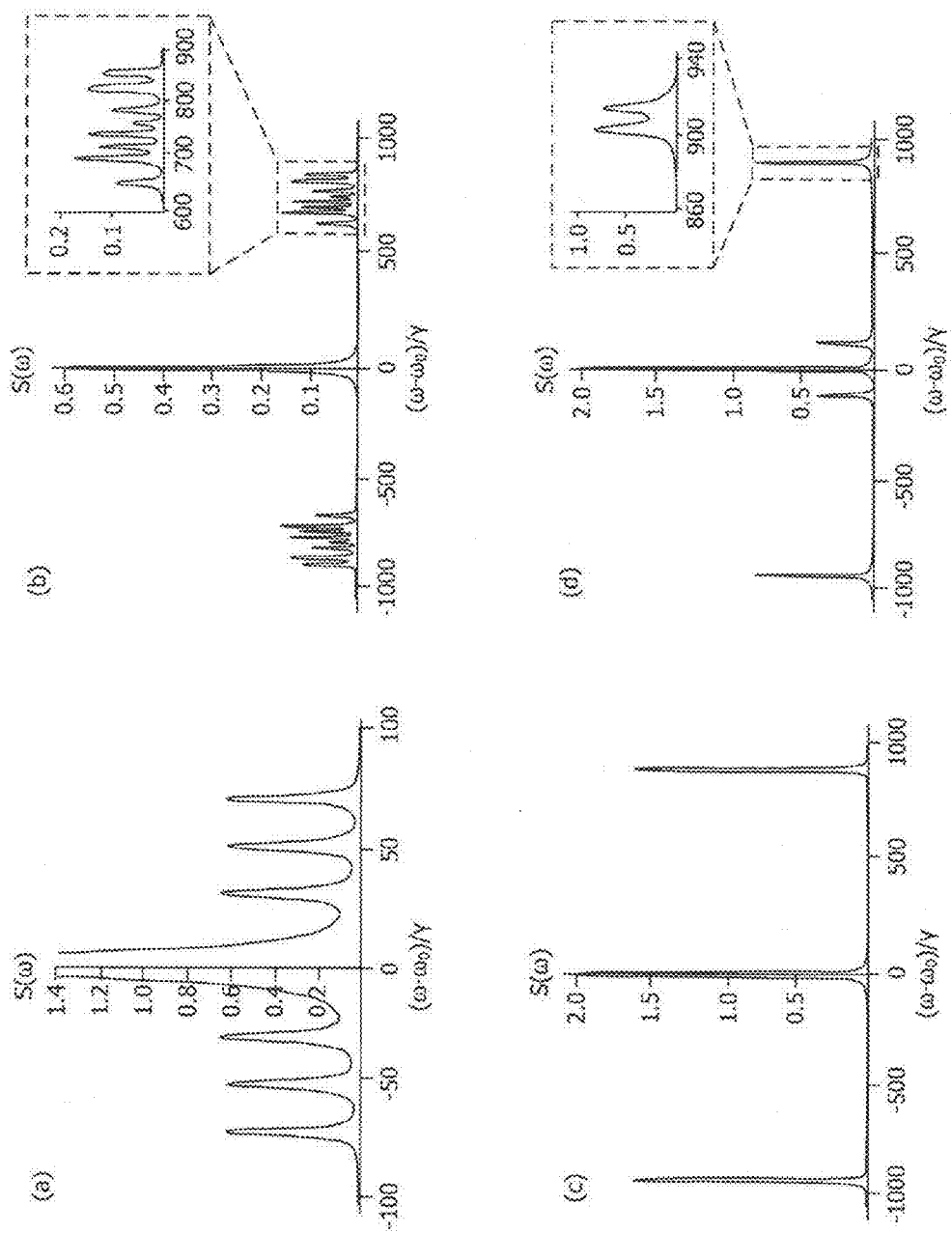
FIG. 3 depicts resonance fluorescence spectra for: a) $x_1=0.3\lambda$, $x_2=0.5\lambda$, $x_3=0.7\lambda$ and $\Omega(x)=100\gamma x/\lambda$; b) $x_1=0.45\lambda$, $x_2=0.5\lambda$, $x_3=0.56\lambda$ and $\Omega(x)=1500\gamma x/\lambda$; c) $x_1=0.485\lambda$, $x_2=0.5\lambda$, $x_3=0.6\lambda$ and $\Omega(x)=1\gamma x/\lambda$; and, d) same as c but with $\Omega(x)=200\gamma x/\lambda$.

For the sidebands, the eigenenergy and eigenvectors of the dressed system may be numerically solved and the allowed transition frequencies calculated. In an actual experiment, the sideband peaks of the spectrum were measured. According to Eq. (13), there are three groups of allowed sideband spectrum on the positive side: $\omega_0 + \Omega_1 \pm \Omega_{12} \pm \Omega_{13}$, $\omega_0 + \Omega_2 \pm \Omega_{12} \pm \Omega_{23}$ and $\omega_0 + \Omega_3 \pm \Omega_{13} \pm \Omega_{23}$. The Rabi frequencies for each atom may be obtained by averaging over each group of the spectrum. For example, if there are three atoms and their positions are $x_1 = 0.3\lambda$, $x_2 = 0.5\lambda$ and $x_3 = 0.7\lambda$, the separation is $\lambda/5$. A gradient electric field is applied such that $\Omega(x) = 100\gamma x/\lambda$. The resonance fluorescence spectrum is shown in FIG. 3a. From the spectrum, the sideband frequencies are $\Omega_1 = (30.00 \pm 1.82)\gamma$, $\Omega_2 = (50.00 \pm 1.82)\gamma$, $\Omega_3 = (70.00 \pm 1.72)\gamma$. The positions of the atoms may be determined as: $x_1 = (0.300 \pm 0.002)\lambda$, $x_2 = (0.500 \pm 0.002)\lambda$, and $x_3 = (0.700 \pm 0.002)\lambda$ which match the previously set parameters very well.

As a second example, consider that the three atoms are located at positions $x_1 = 0.45\lambda$, $x_2 = 0.5\lambda$ and $x_3 = 0.56\lambda$. The shortest distance is $\lambda/20$. A strong gradient electric field is applied such that $\Omega(x) = 1500\gamma x/\lambda$. The resonance fluorescence spectrum is shown in FIG. 3b. From the spectrum, the sideband frequencies may be determined as shown in the following table ($\gamma$):

| |
|---|
| 648.4 ± 2.7 |
| 652.4 ± 2.7 |
| 694.3 ± 2.8 |
| 698.3 ± 2.8 |
| 715.5 ± 2.6 |
| 741.3 ± 2.5 |
| 761.5 ± 2.7 |
| 787.2 ± 2.5 |
| 825.7 ± 2.7 |
| 829.7 ± 2.7 |
| 851.4 ± 2.8 |
| 855.3 ± 2.8 |

Then, the gradient laser field was slightly increased such that $\Omega(x) = 1700\gamma x/\lambda$ and the spectrum peaks are shown in the following table ($\gamma$):

| |
|---|
| 693.6 ± 2.7 |
| 697.4 ± 2.7 |
| 739.5 ± 2.8 |
| 743.3 ± 2.8 |
| 765.4 ± 2.6 |
| 791.2 ± 2.5 |
| 811.4 ± 2.7 |
| 837.2 ± 2.5 |
| 881.7 ± 2.8 |
| 885.5 ± 2.8 |
| 907.4 ± 2.8 |
| 911.3 ± 2.8 |

Comparing these two tables, it is apparent that the separations between peaks in each column do not change significantly. However, the separations between peaks in different columns change significantly. From this result it can be determined that the spectrum from each column belongs to the same group. Averaging over each column of the first table one may obtain $\Omega_1 = (673.35 \pm 2.75)\gamma$, $\Omega_2 = (751.38 \pm 2.58)\gamma$, $\Omega_3 = (840.53 \pm 2.75)\gamma$. The positions of the atoms may then be determined: $x_1 = (0.449 \pm 0.002)\lambda$, $x_2 = (0.501 \pm 0.002)\lambda$, and $x_3 = (0.560 \pm 0.002)\lambda$ which also match the actual positions of the atoms quite well.

If there are two atoms whose distance is smaller than this limit, the method described above may be used. For example, there are three atoms and their positions are $x_1 = 0.485\lambda$, $x_2 = 0.5\lambda$ and $x_3 = 0.6\lambda$. The distance between the first atom and the second atom is $0.015\lambda$ which is less than $\lambda/50$. From Eq. (2), one may calculate that the dipole-dipole interaction energy is $891.92\gamma$ which is very large. In this situation, a weak gradient laser field may be applied first such that the corresponding Rabi frequency is $\Omega(x) = 1\gamma x/\lambda$. The resonance fluorescence spectrum may be solved numerically and the result is shown in FIG. 3c. It can be seen that only two sideband peaks appear and their positions are $\omega = \omega_o \pm 891.90\gamma$ which match very well with the calculation value. From Eq. (2), one may deduce that the distance between these two, close atoms is $\Delta x_{12} = 0.015\lambda$. Then, the gradient laser field may be increased to a medium value, for example $\Omega(x) = 200\gamma x/\lambda$. The numerical result of the corresponding resonance fluorescence spectrum is shown in FIG. 3d. From the spectrum it can be seen that each sideband peak split into two peaks. For example, the positive sideband peak splits into $\omega_0 + 902.72\gamma$ and $\omega_0 + 913.36\gamma$. According to Eq. (14) and Eq. (15), $$\Omega_{12} + \frac{(\Omega_1 + \Omega_2)^2}{2\Omega_{12}} = 913.36\gamma \quad (16)$$

$$\Omega_{12} + \frac{\Omega_1 \Omega_2}{\Omega_{12}} = 902.72\gamma \quad (17)$$

where $\Omega_{12}=1794.84\gamma$. Assuming that $\Omega_1=200\gamma x_1/\lambda$ and $\Omega_2=200\gamma(X_1+\Delta x_{12})/\lambda$, one may get $x_1=0.4816\lambda$ from Eq. (18) and $x_1'=0.4837\lambda$ from Eq. (19). Averaging these two results produces $\bar{x}_1=0.483\lambda$ which is very close to the value $0.485\lambda$ previously set, and the error is about 0.4%. Additionally, there are two sideband peaks observed near the central peaks which read $(\pm 120\pm 2.6)\gamma$. They are the resonance fluorescence from the third atom and its position may be determined to be $(0.600\pm 0.013)\lambda$ which also matches the correct [preselected] value.

Extension to Larger Area and Higher Dimensions

Figure 4:
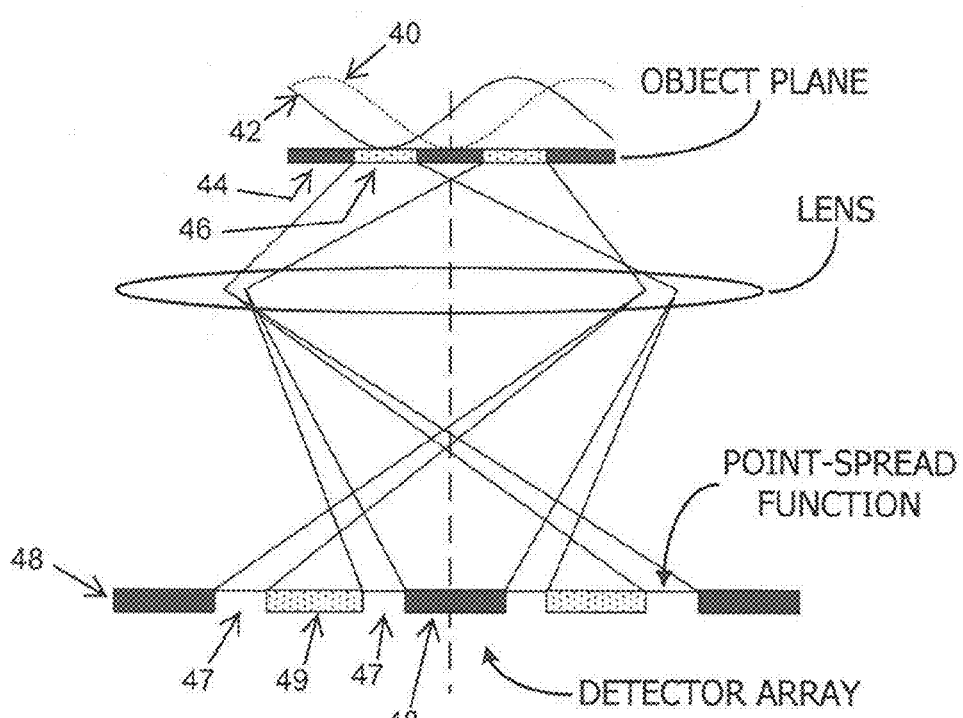
FIG. 4 illustrates a schematic setup for imaging atoms in an extended region based on resonance fluorescence localization microscopy.

Above, it was disclosed how to resolve atoms located within one wavelength. For a region larger than one wavelength, one simple method is to stretch the standing wave with larger periods to cover the entire region. This method is easy to perform, but one disadvantage is that the field intensity increases as the working region increases. If the region is too large, the field will be incredible large. Therefore, for a working region beyond several wavelengths extension, a new way may be needed. One way to extend this limitation is via the divide-and-conquer method. The scheme is shown in FIG. 4. The sample is first exposed to a standing wave denoted by curve 42. The regions designated 44 on the object plane locate in an approximately linear field region while regions 46 do not. The resonance fluorescences are collected by a lens. The fluorescence emitted by regions 44 are focused to detector pixels 48 on the imaging plane, while the fluorescence emitted by regions 46 are focused to detector pixels 49. At this step, only the spectrum of the fluorescence collected by detector pixels 48 are analyzed and the positions of the atoms in regions 44 on the object plane may be determined by the method disclosed above. Then, the standing wave is shifted by a phase $\lambda/2$. At this time, regions 46 locate in an approximately linear field while regions 44 do not. Applying a similar process, the positions of the atoms in regions 46 may be determined. Because the image of a point in the object plane is not a point but a small disk which is usually described by the point spread function of the lens, there may be a gap 47 between neighboring detector pixels (48, 49) to ensure that the fluorescence from regions 44 do not shine on detector pixels 49 and vice versa. If there is an optical detecting array for each working region on the order of several wavelengths, this method is possible.

Figure 5:
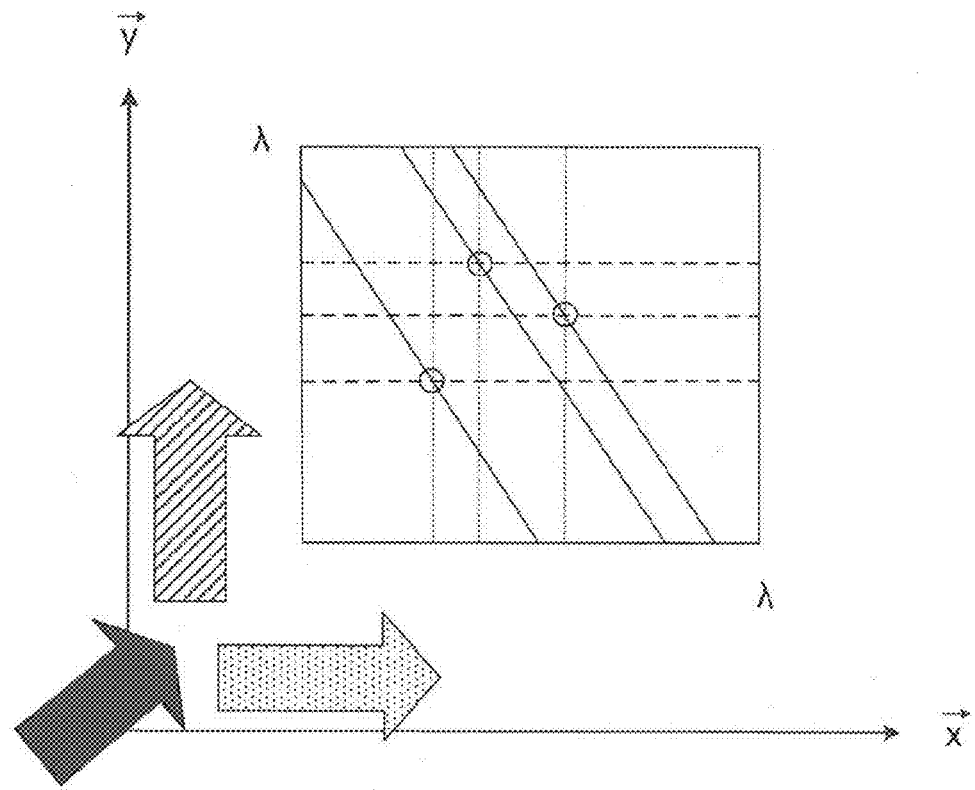
FIG. 5 depicts an example of 2D resonance fluorescence localization microscopy according to the invention.

The method of the present invention may also be applied to a 2D image. Such a scheme is shown in FIG. 5. Three steps are needed to obtain the two dimensional spatial information. In the first two steps, a gradient laser field is shined along the x(y) direction, from the resonance fluorescence spectrum a discrete set of x(y) position information of the atoms may be obtained. After that, the positions of the atoms still cannot be determined because all combinations of x values and y values are possible. One should therefore shine a third gradient field from a direction which avoids any two pairs of (x, y). From the third resonance fluorescence spectrum the positions of the atoms may be determined.

The resonance fluorescence spectrum of a number of two-level atoms is driven by a gradient coherent laser field. In the weak dipole-dipole interaction region (separation less than $\lambda/50$), a very strong laser field may be applied such that the Rabi frequency is much larger than the dipole-dipole interaction energy. From the spectrum the positions of each atom may be determined by just a few measurements. This sub-wavelength microscopy scheme is entirely based on far-field technique and it does not require point-by-point scanning, which makes the method more time-efficient. When two atoms are very close to each other (less than $\lambda/50$), the position information for each atom may still be obtained with very high accuracy provided that they are not too close to other atoms. The method may be extended to an arbitrary large region without requiring more peak laser power and only a few measurements are required.

In the method of the present invention, uncertainty may be due to the linewidth of the spectrum and the calibration of the light intensity. Lower density of atoms within $\lambda/10$ provides narrower linewidth and therefore smaller uncertainty. Good calibration of the light intensity is also required in an experiment in order to extract more precise position information. There is a limitation on the number of atoms within one wavelength which is about 50 in 1D and 2500 in 2D space. Another limitation of the method is that it is still not clear how to extract the spatial information of atoms when more than two atoms are very close to each other (less than $\lambda/50$).

Eigenvalues and Eigenvectors

The eigenvalue and eigenvector for $H_0^i$ are:

$$E_i^+ = \left(n_i - \frac{1}{2}\right)\hbar\omega_0 + \frac{\hbar\Omega_i}{2}, \quad |\Phi_i^+\rangle = \frac{|g_i, n_i\rangle + |e_i, n_i-1\rangle}{\sqrt{2}} \quad (18)$$

$$E_i^- = \left(n_i - \frac{1}{2}\right)\hbar\omega_0 - \frac{\hbar\Omega_i}{2}, \quad |\Phi_i^-\rangle = \frac{|g_i, n_i\rangle - |e_i, n_i-1\rangle}{\sqrt{2}}$$

where $\Omega_i = g\sqrt{n_i}$ and $n_i$ is the mean number of photons that interact with the ith atom. The eigenvalues of $H_0$ are just the summation of the eigenvalues of each atom:

$$E_\alpha^0 = \left(n - \frac{N}{2}\right)\hbar\omega_0 + \frac{\hbar}{2}\sum_i \chi_i^\alpha \Omega_i \quad (19)$$

where $\alpha=1, 2, \ldots, 2^N$, $n=\Sigma_i n_i$ and $\chi_i^\alpha=\pm 1$. The corresponding eigenvectors are:

$$|\alpha\rangle = \frac{1}{\sqrt{2^N}} \bigotimes_{i=1}^{N} (|g_i, n_i\rangle + \chi_i^\alpha |e_i n_i - 1\rangle) \quad (20)$$

which is equivalent to Eq. (2).

The perturbation energy due to the dipole-dipole interaction is:

$$\Delta_\alpha = \langle\alpha|H_{dd}|\alpha\rangle \quad (21)$$

$$= \hbar \sum_{i\neq j} \Omega_{ij}\langle\alpha|S_i^+ S_j^- + S_j^+ S_i^-|\alpha\rangle$$

$$= \frac{\hbar}{4}\sum_{i\neq j}\Omega_{ij}(\langle g_i|+\langle e_i|\chi_i^\alpha)(\langle g_j|+\langle e_j|\chi_j^\alpha)$$

$$(S_i^+ S_j^- + S_j^+ S_i^-)(|g_i\rangle + \chi_i^\alpha|e_i\rangle)(|g_j\rangle + \chi_j^\alpha|e_j\rangle))$$

$$= \frac{\hbar}{4}\sum_{i\neq j}\Omega_{ij}(\langle g_i|+\langle e_i|\chi_i^\alpha)(\langle g_j|+\langle e_j|\chi_j^\alpha)$$

$$(\chi_j^\alpha|e_i\rangle|g_j\rangle + \chi_i^\alpha|g_i\rangle|e_j\rangle))$$

wherein the photon part has been ignored because the dipole-dipole Hamiltonian only depends on atomic operators.

Linewidth

Assume that $|\alpha\rangle \to |\beta\rangle$ is an allowed transition, i.e., $\alpha=\beta$ or they differ from each other by only one term. The relaxation term for the $|\alpha\rangle \to |\beta\rangle$ transition is given by:

$$(L\rho)_{\alpha\beta} = \sum_{i,j=1}^{N} \gamma_{ij} (\langle \alpha | S_i^+ S_j^- \Sigma | \beta \rangle + \langle \alpha | \Sigma S_i^+ S_j^- | \beta \rangle - 2 \langle \alpha | S_j^- \rho S_i^+ | \beta \rangle)$$

For i=j, $$S_i^+ S_i^- | \alpha \rangle = \frac{1}{\sqrt{2^N}} \bigotimes_{k \neq i} (|g_k\rangle + \chi_k^\alpha |e_k\rangle)(\chi_i^\alpha |e_i\rangle) \quad (23)$$

$$= \frac{1}{2}(|\alpha\rangle - |\alpha^i\rangle)$$

$$S_i^+ S_i^- | \beta \rangle = \frac{1}{\sqrt{2^N}} \bigotimes_{k \neq i} (|g_k\rangle + \chi_k^\beta |e_k\rangle)(\chi_i^\beta |e_i\rangle) \quad (24)$$

$$= \frac{1}{2}(|\beta\rangle - |\beta^i\rangle)$$

$$S_i^+ | \alpha \rangle = \frac{1}{\sqrt{2^N}} \bigotimes_{k \neq i} (|g_k\rangle + \chi_k^\alpha |e_k\rangle)|e_i\rangle \quad (25)$$

$$= \chi_i^\alpha \frac{|\alpha\rangle - |\alpha^i\rangle}{2}$$

$$S_i^+ | \beta \rangle = \frac{1}{\sqrt{2^N}} \bigotimes_{k \neq i} (|g_k\rangle + \chi_k^\beta |e_k\rangle)|e_i\rangle \quad (26)$$

$$= \chi_i^\beta \frac{|\beta\rangle - |\beta^i\rangle}{2}$$

where $|\alpha^i\rangle$ and $|\alpha\rangle$ have different sign only on the ith term and $|\beta^i\rangle$ and $|\beta\rangle$ have different sign on the ith term. There are N−1 pairs which satisfy this condition. From (26-29), one may obtain:

$$\sum_i \gamma_{ii} (\langle \alpha | S_i^+ S_i^- \rho | \beta \rangle + \langle \alpha | \rho S_i^+ S_i^- | \beta \rangle - 2 \langle \alpha | S_i^- \rho S_i^+ | \beta \rangle) = \quad (27)$$

$$\frac{\gamma}{2} \sum_i \{[2 - \chi_i^\alpha \chi_i^\beta] \rho_{\alpha\beta} - [1 - \chi_i^\alpha \chi_i^\beta] \rho_{\alpha^i \beta} - [1 - \chi_i^\alpha \chi_i^\beta] \rho_{\alpha \beta^i} - \chi_i^\alpha \chi_i^\beta \rho_{\alpha^i \beta^i} \}$$

$$= \begin{cases} \frac{N\gamma}{2} \rho_{\alpha\beta} - \frac{\gamma}{2} \sum_i \rho_{\alpha^i \beta^i} \\ \frac{(N+2)\gamma}{2} \rho_{\alpha\beta} - \frac{\gamma}{2} \sum_i \rho_{\alpha^i \beta^i} - \rho_{\beta\alpha} - 2\rho_{\beta\beta} - 2\rho_{\alpha\alpha} \end{cases} \quad (28)$$

in which the first equation in Eq. (28) is for α=β, while the second equation is for α≠β but only differs in one term. The last three terms in the second equation may be ignored in the secular approximation because they have a different transition frequency from $\omega_{\alpha\beta}$. The survival of the second term depends on the coupling of the system. If all dipole-dipole interaction energies are small and can be neglected, the second term survives because $\omega_{\alpha^i\beta^i} = \omega_{\alpha\beta}$ and there are N−1 terms. When the calculation of Eq. (30) is repeated for other transitions, one may find that $\rho_{\alpha\beta}$ appears one time with coefficient $(N+2)\gamma/2$ and N−1 times with coefficient $-\gamma/2$. Therefore when the summation over the whole set is performed, one may find that the coefficient of $\rho_{\alpha\beta}$ is $(N+2)\gamma/2 - (N-1)\gamma/2 = 3\gamma/2$ which is exactly the linewidth of the independent atoms. However, if all dipole dipole interaction cannot be neglected, then the second term goes away in the secular approximation due to $\omega_{\alpha^i\beta^i} \neq \omega_{\alpha\beta}$ and the linewidth in this case is $(N+2)\gamma/2$.

In Eq. (25), spontaneous emission terms (i≠j) have also been correlated. These terms appear only when the dipole-dipole interaction cannot be neglected. If an extreme case wherein all dipole dipole interaction cannot be neglected and no spectrum is overlapped, one has:

$$S_j^+ S_i^- | \alpha \rangle = \frac{1}{\sqrt{2^N}} \bigotimes_{k \neq i,j} (|g_k\rangle + \chi_k^\alpha |e_k\rangle)(\chi_i^\alpha |g_i\rangle)|e_j\rangle \quad (29)$$

$$= \frac{1}{4} \chi_i^\alpha \chi_j^\alpha |\alpha\rangle + \ldots$$

$$S_j^+ S_i^- | \beta \rangle = \frac{1}{\sqrt{2^N}} \bigotimes_{k \neq i,j} (|g_k\rangle + \chi_k^\beta |e_k\rangle)|e_i\rangle\langle \chi_i^\beta | g_i \rangle \quad (30)$$

$$= \frac{1}{4} \chi_i^\beta \chi_j^\beta |\beta\rangle + \ldots$$

$$S_j^+ | \alpha \rangle = \frac{1}{\sqrt{2^N}} \bigotimes_{k \neq j} (|g_k\rangle + \chi_k^\alpha |e_k\rangle)|e_j\rangle \quad (31)$$

$$= \frac{\chi_i^\alpha}{2} |\alpha\rangle + \ldots$$

$$S_i^+ | \beta \rangle = \frac{1}{\sqrt{2^N}} \bigotimes_{k \neq i} (|g_k\rangle + \chi_k^\beta |e_k\rangle)|e_j\rangle \quad (32)$$

$$= \frac{\chi_i^\beta}{2} |\beta\rangle + \ldots$$

where ... denote terms that have different transition frequencies from $\omega_{\alpha\beta}$ and they can be neglected in the secular approximation. Then:

$$\sum_{i \neq j} \gamma_{ij} (\langle A | S_i^+ S_j^- \rho | \beta \rangle + \langle \alpha | \rho S_i^+ S_j^- | \beta \rangle - 2 \langle \alpha | S_j^- \rho S_i^+ | \beta \rangle) = \quad (33)$$

$$\sum_{i \neq j} \frac{\gamma_{ij}}{4} [\chi_i^\alpha \chi_j^\alpha + \chi_i^\beta \chi_j^\beta - 2\chi_j^\alpha \chi_i^\beta] \rho_{\alpha\beta} + \ldots =$$

$$\left\{ \sum_{i \neq j \neq p} \frac{\gamma_{ij}}{4} [\chi_i^\alpha \chi_j^\alpha + \chi_i^\beta \chi_j^\beta - 2\chi_j^\alpha \chi_i^\beta] + \sum_{j \neq p} \frac{\gamma_{pj}}{4} [\chi_p^\alpha \chi_j^\alpha + \chi_p^\beta \chi_j^\beta - 2\chi_j^\alpha \chi_p^\beta] + \sum_{i \neq p} \frac{\gamma_{ip}}{4} [\chi_i^\alpha \chi_p^\alpha + \chi_i^\beta \chi_p^\beta - 2\chi_p^\alpha \chi_i^\beta] \right\}$$

$$\rho_{\alpha\beta} + \ldots = 0$$

The first summation vanishes because $\chi_i^\alpha = \chi_i^\beta$ and $\chi_j^\alpha = \chi_j^\beta$ for i,j≠p. Because $\chi_p^\alpha = -\chi_p^\beta$ and $\chi_j^\alpha = \chi_j^\beta$, the first two terms in the second summation drop out. Similarly, the first two terms of the third summation also drop out. The remaining terms in the second summation and the third summation are just opposite because $$\sum_{j \neq p} \frac{\gamma_{pj}}{4} [-2\chi_j^\alpha \chi_p^\beta] = \sum_{i \neq p} \frac{\gamma_{pi}}{4} [-2\chi_i^\alpha \chi_p^\beta] = \sum_{i \neq p} \frac{\gamma_{pi}}{4} [+2\chi_i^\beta \chi_p^\alpha] \quad (34)$$

When the first order correction of the wavefunction is considered, this correlated spontaneous emission rate is non-zero. However their values are on the order of $(\Omega_{ij}/\Omega_i)^2$ which may be assumed to be very small.

Although particular embodiments of the present invention have been shown and described, they are not intended to limit what this patent covers. One skilled in the art will understand that various changes and modifications may be made without departing from the scope of the present invention as literally and equivalently covered by the following claims.

What is claimed is:

1. A method for determining the positions of a plurality of two-level atoms located in a line comprising:
    shining two, linear-polarized laser fields on atoms trapped in a quantum dot from opposite directions such that a standing wave is formed;
    monitoring the resonance-fluorescence photons emitted by the trapped atoms;
    obtaining the Rabi frequencies from the sideband peaks in the resulting fluorescence spectrum;
    calculating the positions of the trapped atoms from the Rabi frequencies.

2. A method as recited in claim 1 wherein the atoms are identical atoms.

3. A method as recited in claim 1 wherein the atoms are located within one wavelength of the laser fields.

4. A method as recited in claim 1 further comprising stretching the standing wave such that the sample is located within the linear region between the node and antinode.

5. A method as recited in claim 1 further comprising detecting fluorescence photons with a detector in the z direction when the atoms are located in a line along the x axis.

6. A method as recited in claim 1 wherein far-field optical microscopy is used to obtain the resonance fluorescence spectrum.

7. A method for determining the positions of a number of two-level atoms in two dimensions (x,y) comprising:
    shining a first gradient laser field along the x-axis direction;
    obtaining a discrete set of x-axis position information of the atoms from the resulting first resonance fluorescence spectrum;
    shining a second gradient laser field along the y-axis direction;
    obtaining a discrete set of y-axis position information of the atoms from the resulting second resonance fluorescence spectrum;
    shining a third gradient field from a direction which avoids any two pairs of (x,y); and,
    determining the positions of the atoms from the resulting third resonance fluorescence spectrum.

8. A method as recited in claim 7 wherein far-field optical microscopy is used to obtain the resonance fluorescence spectra.

9. A method for determining the positions of a plurality of two-level atoms located in a line comprising:
    shining two, linear-polarized laser fields on atoms trapped in nitrogen vacancy centers in diamond from opposite directions such that a standing wave is formed;
    monitoring the resonance-fluorescence photons emitted by the trapped atoms;
    obtaining the Rabi frequencies from the sideband peaks in the resulting fluorescence spectrum;
    calculating the positions of the trapped atoms from the Rabi frequencies.

10. A method for determining the positions of a plurality of two-level atoms located in a line comprising:
    shining two, linear-polarized, gradient laser fields on the atoms from opposite directions such that a standing wave is formed;
    monitoring the resonance-fluorescence photons emitted by the atoms;
    obtaining the Rabi frequencies from the sideband peaks in the resulting fluorescence spectrum;
    calculating the positions of the atoms from the Rabi frequencies.

11. A method as recited in claim 10 further comprising changing the gradient of the laser field by a certain amount.

12. A method as recited in claim 10 further comprising applying a first, weaker gradient field and subsequently applying a second, stronger gradient field.

13. A method as recited in claim 12 wherein the second, stronger gradient field is less than the dipole-dipole interaction energy of the atoms.

14. A method for determining the positions of a plurality of two-level atoms located in a line comprising:
    shining two, linear-polarized laser fields on the atoms from opposite directions such that a standing wave is formed;
    monitoring the resonance-fluorescence photons emitted by the atoms;
    obtaining the Rabi frequencies from the sideband peaks in the resulting fluorescence spectrum;
    calculating the positions of the atoms from the Rabi frequencies; and,
    averaging the results when two results are obtained for the positions of each atom.

* * * * *